United States Patent
Klatzmann

(10) Patent No.: US 6,383,807 B1
(45) Date of Patent: *May 7, 2002

(54) METHOD OF TRANSFORMING T LYMPHOCYTES

(75) Inventor: David Klatzmann, Paris (FR)

(73) Assignee: Universite Pierre et Marie Curie, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,557

(22) Filed: Nov. 18, 1999

Related U.S. Application Data

(63) Continuation-in-part of application No. 08/482,799, filed on Jun. 7, 1995, now Pat. No. 6,048,525, which is a continuation of application No. 08/084,242, filed on Nov. 9, 1993.

(30) Foreign Application Priority Data

Oct. 30, 1991 (FR) .............................. 91 13430

(51) Int. Cl.⁷ .......................... C12N 5/08; C12N 15/00; C12N 15/09; C12P 21/06; A01N 63/00

(52) U.S. Cl. ................................ 435/372.3; 435/320.1; 435/69.1; 424/93.21

(58) Field of Search .............................. 424/93.21, 93.2; 435/372.3, 320.1, 325, 69.1; 514/44

(56) References Cited

PUBLICATIONS

L. K. Venkatesh et al. Selective induction of toxicity to human cells expressing human immunodeficiency virus type 1 tat by a conditionally cytotoxic adenovirus vector.*

* cited by examiner

Primary Examiner—Remy Yucel
Assistant Examiner—Konstantina Katcheves
(74) Attorney, Agent, or Firm—Brown Rudnick Berlack Israels, LLP; Mark A. Hofer

(57) ABSTRACT

The present invention discloses a method for transforming hematopoietic cells, in particular, T lymphocytes. The method involves co-culturing target cells, such as T lymphocytes, with pseudo-viral particles comprising a foreign DNA sequence.

11 Claims, No Drawings

METHOD OF TRANSFORMING T LYMPHOCYTES

RELATED APPLICATION

The present Application is a continuation-in-part of Application No. 08/482,799, filed Jun. 7, 1995, now U.S. Pat. No. 6,048,525, which is a continued prosecution application of U.S. Ser. No. 08/084,242, filed Nov. 9, 1993, which claims priority to French application No. PCT/FR92/0106, filed Oct. 30, 1992.

The invention relates to cells designed as traps for antigens causing dysfunctions of the immune system, more particularly those which are implicated in naturally occurring (auto-immune diseases) or induced (grafts) dysfunctions of the immune system.

The invention relates more particularly to the provision of medicines for the prevention of diseases of the "Graft versus Host Diseases" (GVHT) (diseases due to the reaction of a transplant against the host) or for the treatment of auto-immune diseases, more particularly in association with the said cells designed as traps.

In what follows the expression "antigen" relates to all substances or all products against which tolerance on the part of the host is desired, althou; they would naturally tend to induce a defensive reaction or one of rejection on the part of the immune system of the host.

The objective of the invention is to remedy these deficiencies, more particularly to provide a different therapeutic approach based on the presence, ensured beforehand in the host, of lymphoid cells, in particular T lymphocytes trapped against an activation by the antigens with respect which tolerance is sought.

The invention thus relates more particularly to a population of hematopoietic cells, designed as traps to prevent an activation by antigens normally foreign to the host but with respect to which tolerance is desired, characterized in that these cells contain a genetic sequence, the expression product of which is able, when its production is enhanced to give a sufficient quantity of it within the cell traps, to react in situ with a pharmaceutically active substance to induce the destruction of these cells, and means specifically inducible by an activation signal supplied to these cells by the antigen to trigger the above-mentioned enhanced production.

The administration of such a pharmaceutically active substance to a host carrying. such a population of cell traps, can provide for the effic ient protection of the host against an activation by antigens of the appropriate specific lymphoid cells of the immune system, in particular of its T lymphocytes, as a result of the destruction of these lymphoid cells even before they have begun to divide. As a result of the destruction of the cell traps carried out at the command of the antigen itself, their division will be blocked.

Generally speaking the procedures used up to now to confront the diseases resulting from an intolerance on the part of the immune system tend either to cause a generalized immunodepression in the host or modify some classes of the cells affected by this type of antigen, in a manner such as to confer on them the capacity to produce constitutively certain substances which are supposed to inhibit the development of such antigens.

The invention relates more particularly to a population of cells of the bone marrow, in particular imnature cells which can be used for bone marrow grafts, these cells being "designed as traps" under the conditions indicated above.

The invention thus also relates to the use for the production of medicines active against diseases of the GVHT type of a pharmaceutically active molecule which is able, when it is associated in vivo with a population of cells, in particular hematopoietic cells, designed as traps in the sense described above and reintroduced into the organism of the host, in particular subsequent to a bone marrow graft, to interact with the expression product of the genetic sequence contained in these cell traps to cause their destruction as soon as they are stimulated by the antigens against which tolerance is desired.

In a preferred embodiment of the invention, the population of cell traps is characterized in that the As providing for the specific triggering of the enhanced production of the expression product and the genetic i@sequence mentioned above are contained in a recombinant DNA sequence contained in these cells. Advantageously, the agents specifically inducible by a signal resulting from the activation of these cells by these antigens consist of regulatory sequences normally controlling the expression of a cytokine, in particular a lymphokine, for example interleukin 2, or the expression of receptors corresponding to this cytokine, in particular the interleukin 2 receptor, and the above-mentioned genetic sequence is then placed under the control of this promoter and codes for an expression product which is able, when its production is enhanced as a result of the activation of the above-mentioned regulatory sequences, to react with a pharmaceutically active substance to form a reaction product capable of inducing directly or indirectly the destruction of the cells in the process of being activated.

Advantageously, the regulatory sequence used is constituted by a promoter normally associated with interleukin 2 or preferably with an interleukin 2 receptor. In particular, recourse will be bad to the promoter for the alpha chain of the interleukin 2 receptor (sequence described in Cell, April 1987). When activated, this promoter leads to an amplified expression of the sequence placed under its control (in particular in JURKAT cells) which is of the order of 30 times that which is measured when it is not activated.

Advantageously, the pharmaceutical substance used induces directly or indirectly the interruption in situ of the replication of DNAs within the cells in question. In a manner also particularly preferred, the invention also makes use of the procedure called "obliteration by thymidine kinase" already described by Borelli et al. (1988) in cells already expressing it constitutively and in a different field of application. The population of cell traps conforming to a preferred embodiment of the invention is then characterized in that the expression product encoded in the said genetic sequence placed under the control of the said promoter is a molecule such as the thymidine kinase of the Herpes simplex virus 1 (HSV1-TK) which is able, when it is present at a sufficient concentration in the cells in question, to phosphorylate nucleoside analogues, such as acyclovir (9-/(2-hydroxyethoxy)methyl/guanine or gancyclovir (9-[1,3-10 hydroxy-2-propoxymethyl] guanine), to give the monophosphate derivatives, which can themselves be converted by cellular enzymes into nucleoside triphosphates which can be incorporated into nucleic acids in the course of chain elongation brought about by polymerases within the said cells, resulting in the interruption of the elongation of the chains and cell death which follows.

It will be apparent immediately that the "active pharmaceutical substance" utilisable in a therapeutic protocol which makes use of one of the preferred different populations of cell traps such as defined above must, in each case, exhibit the properties which will allow it to react with the corresponding expression product under the conditions which have been defined.

The invention in fact takes advantage of two distinct phenomena:
1) the expression of a toxic gene placed under the control of a promoter for a cytokine or a cytokine receptor in cell traps conforming to the invention is at the mst very low as long as they are not activated by the antigen in question;
2) the induction of the expression of the toxic genetic sequence may be made sufficiently rapid in those of the cell traps which are activated to trigger their destruction even before the first cell divisions of these cells occur. Consequently, the actlivation of the immune system of the host is blocked in its initial phase, when it is stimulated by an antigen towards which tolerance is in fact desired.

In order to construct for use in man—or, optionally, in animals—the cell traps conforming to the invention, recourse may be had to any adequate procedure, in particular by in vitro infection of the corresponding cells by a pseudo-viral particle of the amphotropic Moloney type, which thus also infects human cells. These viral particles are produced by a socalled "packaging" cell line which will have been constructed beforehand. A packaging line is capable of producing all of the structural elements which constitute a viral particle, but is incapable of introducing into viral particles in the process of maturation the viral RNAs produced by this cell line. That is why these so-called packaging lines continually produce empty viral particles. The introduction of a suitable genetic construction which contains the recombinant DNA such as that defined above makes it possible for these packaging lines to be introduced into the empty viral particles thus creating pseudo-viral particles. These pseudo-viral particles are capable of infecting different target cells, target cells which vary according to the packaging cell used initially. For example, if this packaging line is derived from a so-called amphotropic Moloney virus, the viral particles produced are able to infect human hematopoietic cells.

Thus, the cells designed to be traps, in particular hematopoietic cells, are themselves placed in the presence of a culture supernatant derived from the packaging line which produces the amphotropic pseudo-viral particles. The cells designed to be traps are, for example, co-cultured directly with the packaging cells. During this step of culture or co-culture, the ampbotropic particles present in the suspension infect the cells designed to be traps and thus introduce into the latter the genetic elements which they contain.

For the production of these cell traps which make use more particularly of a promoter of a lymphokine or lymphokine receptor, it will be advantageous to have recourse to the amphotropic murine retroviral vectors and to packaging cell lines (sudi as those which were reviewed by Weatherall, 1991 and Friedman, 1989, respectively). The procedures for the production of cell lines trannsformed by such a retroviral vector (see, for example, Danos et al., 1988 and Markowitz et al., 1989), may be transposed to the production of hematopoietic cell traps conforming to the invention. Similarly, the genetic transfer procedures which make use of such systems (Kasid et al., 1990) may also be applied to the trasfer to man of cell traps such as those which have been defined above.

A useful population of cell. traps conforming to the invention is derived from immature bone marrow cells, obtained from a sample of bone marrow, which in particular lack the surface markers which characterize mature hematopoietic cells, and transformed beforehand into "cell traps" under the above-mentioned conditions. They are particularly suited to the implementation of one of the treatment protocols, the steps of which are briefly recalled below.

The essential steps of this protocol are the following:

taking of a bone marrow sample from the patient and treatment of this bone marrow acording to the state of the art procedures so as to purify the immature stem cells;

incorporation into these immature cells of the above-mentioned recombinant DNA containing the promoter which can be activated by the antigen and, placed under the control of this promoter, the genetic sequence coding for example, for HSV1-TK, the expression product of which can interact with the pharmaceutically active substance subsequently administered, in this case suitable analogues of nucleosides of the acyclovir or gancyclovir type in order to block the activation by the antigen of the cells infected by this antigen;

the bone marrow cells obtained, which then cow the recombinant DNA defined above are ither reinjected in their entirety into the patient or are subjected to an additional step of culture and selection in order to obtain a quantity of cells which have in fact been infected by the amphotropic particles and hence contain and express the genetic information contained in the pseudo-viral particles. The treated bone marrow cells are reinjected by the intravenous route into the patient who will have been conditioned beforehand, for example, by treatment with high concentrations of suitable antiviral drugs used in high doses even if these latter are relatively toxic for the bone marrow since the patient will subsequently receive new bone marrow cells. This prior conditioning of the patient may even imply an in vivo destruction of his original immune system, in particular by irradiation. In this last eventuality, the cell traps reinjected—or the cell traps obtained from a bone marrow taken from a different donor, treated as indicated above and injected into the patient are then capable of renewing themselves constantly in man and of giving rise to the different classes of hematopoietic cells which then all carry the recombinant sequence;

administration of the pharmaceutically active substance to the patient for the time and at the moment required, in particular to bring about the selective destruction of the cell traps, when these latter are activated by the antigen, subsequent to the interaction of the pharmaceutically active substance with the expression product, in particular HSV1-K, then produced in situ in sufficient concentration in these cell traps as a result of the activation of the promoter, in particular that usually associated with an interleukin 2 or an interleukin 2 receptor.

Naturally, the choice of the moment of administration, in particular for example in relation to an organ transplant or foreign bone marrow in the host, as well as the modes of administration of the pharmaceutically active substance, in particular acyclovir or gancyclovir, must be determined by the clinician. They comprise, for example, a continuous treatment initially, and iterative treatments thereafter.

It will be realised that the invention possesses many advantages, in particular in that it is possible for the clinician to control at the same time the triggering, at the moment of his choice , of the interaction of the expression product of the coding sequence with the pharmaceutically active substance administered to those of the cells whose promoter is activated by the antigen or the antigens;

the interruption at the desired moment of the above-mentioned interaction due to discontinuation of the administration of the drug if necessary, the reinstatement of the treatment, also at the time desired.

Examples of the conditions for the implementation of the invention are also given below, naturally in a non-limiting sense.

A. Use for the Preventive Treatment of the Reaction of a Graft Against the Host

In the context of a bone marrow transplantation, in particular when the transplantation is performed in the absence of a total compatibility between the donor and recipient, the bone marrow sample taken from the donor is treated as indicated previously. The genetic construction present in the pseudo-viral particles contains the suicide gene under the control of the promoter of the gene coding for interleukin 2 or the promoter of the gene coding for the interleukin 2 receptor.

The recipient of the bone marrow is irradiated before the reinjection of the bone marrow. Be would then be treated in a preventive manner with acyclovir or any similar drug throughout the entire duration of the immunological reconstitution. It would be possible to perform the treatment in a continuous or discontinuous manner. Thus if some cells derived from the bone marrow graft are sensitized by the antigens of the recipient (GVH reaction), they will then be eliminat as a result of the treatment. Once immunological reconstitution has been obtained, the treatment can be discontinued since in principle all of the potentially dangerous cells will have been eliminated. Nonetheless, during the subsequent evolution of the graft, any possible reactivation of a reaction of the grafted tissue against the host which would be diagnosed as such could be treated by the nucleoside analogues with the same beneficial effect.

B. Use for the Treatment of Auto-immune Diseases

In the case of auto-immune diseases, the situation is very similar to that described previously, except that the bone marrow is derived from the same individual. In this type of therapy, the bone marrow is taken directly from the patient and after a treatment identical with that previously described, it is reinjected into the previously irradiated patent. The reconstitution is then obtained rapidly and in the event of any symptom of auto-immunity, the patient is treated by the nucleoside analogues. For example, for patients suffering from rheumatic diseases of the auto-immune type, the reappearance of rheumatic-type clinical symptoms might entail the reinstatemnt of the treatment with the nucleoside analogues. In principle, it is quite imaginable that this treatment would lead to the definitive elimination of all of the potentially autoreactive cells. Nonetheless, were this not the case, each time that the clinical symptoms would reappear, the treatment would be reinstated.

The invention is not limited to the embodiments which have been more particularly illustrated in the examples, in particular those involving the pair of elements formed respectively by the genetic sequence coding for the HSV1-TK andfthe "pharmaceutically active substance" constituted by acyclovir or an inalogue of this modified nucleoside.

The specialist skilled in the art is capable of imagining other "pairs" of reagents which can be used for the same purposes. One example should be cited, only as an example, this pair thus comprising:

a genetic sequence coding for a defined protease capable of cleaving an "inert" fusion protein resulting from the linking of a toxin, such as a toxic subunit of diphtheria toxin, to another protein through the intermediary of an amino acid sequence constituting a site specifically cleavable by this defined protease provided that this protease is expressed in situ at a concentration exceeding a defined threshold;

a "pharmaceutically active substance" constituted by the said "inert" fusion protein.

The activation of the cell traps contaig such a genetic sequence, placed for example under the control of a promoter for an interleukin 2 receptor, in particular when they are activated by the antigen concerned, would consequently entail the production of the defined protease and, in the presence of the fusion protein introduced into the cells via its administration to the host, an in situ cleavage of this fusion protein and release of the toxic toxin then capable of selectively destroying the activated cell.

What is claimed is:

1. A method of transforming hematopoietic cells which comprise T lymphocytes, said method comprising the steps of:

(a) providing viral particles comprising a foreign nucleic acid sequence which comprises:
(i) a regulatory nucleic acid sequence which is expressable in T lymphocytes and which can be activated by a signal supplied to said T lymphocytes by an antigen that induces graft versus host disease, and
(ii) a nucleic acid sequence that encodes a product which, when contacted in situ with a pharmaceutical substance, reacts with said substance to induce destruction of said T lymphocytes, wherein said nucleic acid sequence is operably linked to said regulatory nucleic acid sequence; and (b) culturing said viral particles, under conditions suitable for cell culturing, with said T lymphocytes, thereby transforming said T lymphocytes with said foreign nucleic acid sequence.

2. The method of claim 1, wherein said regulatory sequence is an interleukin-2 promoter or an interleukin-2 receptor promoter.

3. The method of claim 1, wherein said viral particles are arnphotropic Moloney virus particles produced by a packaging cell line.

4. The method of claim 1, wherein said product, when reacted with said pharmaceutical substance, induces an interruption of DNA replication in said T lymphocytes.

5. The method of claim 4, wherein said product is thymidine kinase.

6. A method of transforming hematopoietic cells which comprise T lymphocytes, said method comprising the steps of:

(a) providing viral particles comprising a foreign nucleic acid sequence which comprises:
(i) a regulatory nucleic acid sequence which is expressable in T lymphocytes and which can be activated by a signal supplied to said T lymphocytes by an antigen that induces graft versus h6st disease, and
(ii) a nucleic acid sequence that encodes thymidine kinase which is operably linked to said regulatory nucleic acid sequence; and (b) culturing said viral particles, under conditions suitable for cell culturing, with said T lymphocytes, thereby transforming said T lymphocytes with said foreign nucleic acid sequence.

7. A method of transforming hematopoietic cells which comprise T lymphocytes, said method comprising the steps of:

(a) providing amphotropic retroviral particles comprising a foreign nucleic acid sequence which comprises:
  (i) a regulatory nucleic acid sequence which is capable of expression in T lymphocytes and which can be activated by a signal supplied to said T lymphocytes by an antigen that induces graft versus host disease, and
  (ii) a nucleic acid sequence that encodes a product which, when contacted in situ with a pharmaceutical substance, reacts with said substance to induce destruction of said T lymphocytes, wherein said nucleic acid sequence is operably linked to said regulatory nucleic acid sequence; and
(b) culturing said amphotropic retroviral particles, under conditions suitable for cell culturing, with said T lymphocytes, thereby transforming said T lymphocytes with said foreign nucleic acid sequence.

8. A population of T lymphocytes comprising a foreign nucleic acid sequence, wherein said foreign nucleic acid sequence comprises a regulatory nucleic acid sequence which is expressed by an activation signal supplied to said T lymphocytes by an antigen that induces graft versus host disease, and a nucleic acid sequence that encodes a product which, when contacted in situ with a pharmaceutical substance, reacts with said substance to induce destruction of said T lymphocytes, wherein said nucleic acid sequence is operably linked to said regulatory nucleic acid sequence.

9. The population of T lymphocytes of laim 8, wherein said regulatory nucleic acid sequence is an interleukin-2 promoter or an interleukin-2 receptor promoter.

10. The population of T lymphocytes of claim 8, wherein said product, when reacted with said pharmaceutical substance, induces an interruption of DNA replication in said T lymphocytes.

11. The population of T lymphocytes of claim 10, wherein said product is thymidine kinase.

* * * * *